United States Patent
Dumeignil et al.

(10) Patent No.: US 9,701,615 B2
(45) Date of Patent: Jul. 11, 2017

(54) METHOD FOR SYNTHESISING ESTERS

(71) Applicants: PIVERT, Venette (FR); Centre National de la Recherche Scientifique (CNRS), Paris (FR); UNIVERSITÉ DES SCIENCES ET TECHNOLOGIES DE LILLE 1, Villeneuve d'Ascq (FR); ECOLE CENTRALE DE LILLE, Villeneuve D'ascq (FR)

(72) Inventors: Franck Dumeignil, Fretin (FR); Simon Desset, Lille (FR); Sébastien Paul, Thun Saint Amand (FR); Guillaume Raffa, Les Halles (FR); Lei Zhang, Villeneuve D'ascq (FR)

(73) Assignees: PIVERT (FR); Centre National de la Recherche Scientifique (CNRS) (FR); UNIVERSITÉ DES SCIENCES ET TECHNOLOGIES DE LILLE 1 (FR); ECOLE CENTRALE DE LILLE (FR)

( * ) Notice: Subject to any disclaimer, the term of this patent is extended or adjusted under 35 U.S.C. 154(b) by 0 days.

(21) Appl. No.: 15/035,447

(22) PCT Filed: Nov. 6, 2014

(86) PCT No.: PCT/FR2014/052840
§ 371 (c)(1),
(2) Date: May 9, 2016

(87) PCT Pub. No.: WO2015/067900
PCT Pub. Date: May 14, 2015

(65) Prior Publication Data
US 2016/0289162 A1 Oct. 6, 2016

(30) Foreign Application Priority Data
Nov. 8, 2013 (FR) ..................... 13 60982

(51) Int. Cl.
C07C 67/40 (2006.01)
C07C 29/149 (2006.01)
C07C 67/00 (2006.01)
C07F 15/00 (2006.01)

(52) U.S. Cl.
CPC ............ *C07C 67/40* (2013.01); *C07C 29/149* (2013.01); *C07C 67/00* (2013.01); *C07F 15/0046* (2013.01)

(58) Field of Classification Search
None
See application file for complete search history.

(56) References Cited

FOREIGN PATENT DOCUMENTS

WO 2013171302 A1 11/2013

OTHER PUBLICATIONS

Denis Spasyuk, et al., "Acceptorless Dehydrogenative Coupling of Ethanol and Hydrogenation of Esters and Imines", © 2012 American Chemical Society—Organometallics 2012, 31, pp. 5239-5242.
Zhang, et al., "Facile Conversion of Alcohols into Esters and Dihydrogen Catalyzed by New Ruthenium Complexes", J. Am. Chem. Soc. 2005, 127, 10840-10841.
Piccirilli, et al., "Hydrogénation sélective de l'oléate de méthyle en alcool oléique en présence de catalyseurs ruthénium-étain supportés", Bulletin de la Société chimique de France 132(11):1109-1117—Dec. 1994, pp. 1109-1117.
Bertoli, et al., "Osmium and Ruthenium Catalysts for Dehydrogenation of Alcohols", © 2011 American Chemical Society, Organometallics 2011, 30, 3479-3482.
Gnanaprakasam, et al., "Ruthenium Pincer-Catalyzed Acylation of Alcohols Using Esters with Liberation of hydrogen under Neutral Conditions", Advanced Synthesis & Catalysis, vol. 352, Issue 18, pp. 3169-3173, Dec. 17, 2010.
Nielsen, et al., "Towards a Green Process for Bulk-Scale Synthesis of Ethyl Acetate: Efficient Acceptorless Dehydrogenation of Ethanol", Angew. Chem. Int. Ed. 2012, 51, 5711 -5713.

*Primary Examiner* — Yate K Cutliff
(74) *Attorney, Agent, or Firm* — St. Onge Steward Johnston & Reens, LLC

(57) ABSTRACT

A method for synthesising a second ester from a first ester, the method including the following steps: a) placing a first ester and a catalyst in the presence of dihydrogen such as to obtain a first alcohol and a second alcohol; b) extracting the second alcohol from the reaction medium; c) reacting the first alcohol with the catalyst of step a) in order to obtain a second ester and dihydrogen; and d) recirculating the dihydrogen obtained in step c) by injecting same into step a).

20 Claims, No Drawings

METHOD FOR SYNTHESISING ESTERS

FIELD OF THE INVENTION

The invention relates to a method for synthesizing esters from biobased starting products by dehydrogenative coupling in the presence of a catalyst. The starting products may be biobased esters such as fatty acid methyl esters (FAMEs) derived from oleaginous materials, for example methyl oleate.

BACKGROUND OF THE INVENTION

Many esters, and especially ethyl acetate, are synthesized on the industrial scale by using starting products of fossil origin (ethylene in the case of ethyl acetate) via multi-step methods. The global market for ethyl acetate was 2.5 million tonnes/year in 2008.

It is known to use a ruthenium-based catalyst to carry out the dehydrogenative coupling of ethanol using for example carbonylchlorohydrido[bis(2-diphenylphosphinoethy-pamino]ruthenium(II), of formula A, (CAS: 1295649-40-9), Trade Name: Ru-MACHO, or D (see below) (cf. M. Nielsen, H. Junge, A. Kammer and M. Beller, *Angew. Chem. Int. Ed.,* 2012, 51, 5711-5713 and EP 2 599 544 A1) or trans-RuCl$_2$(PPh$_3$)[PyCH$_2$NH(CH$_2$)$_2$PPh$_2$], of formula B, (cf. D. Spasyuk and D. Gusev, *Organometallics,* 2012, 31, 5239-5242). These catalysts A and B however require the presence of tBuOK or EtONa in order to be active. The catalyst D requires a long reaction time and a high catalytic loading in order to obtain yields of at most 90% ester.

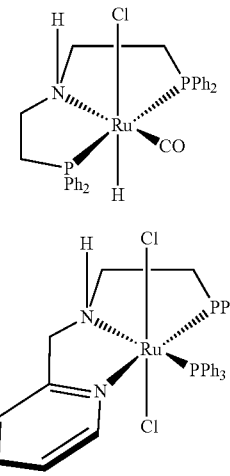

Another catalyst used for the same reaction is the carbonylhydrido(tetrahydroborato)[bis(2-diphenylphosphino-ethyl)amino]ruthenium(II) catalyst of formula C (CAS: 1295649-41-0), Trade Name: Ru-MACHO-BH. This reaction is described in patent application WO 2012/144650 where this synthesis requires the presence of a hydrogen acceptor such as a ketone, for example 3-pentanone. In addition to dissolving the various species (catalyst and substrate), 3-pentanone acts as a hydrogen acceptor. Thus, an at least stoichiometric amount of 3-pentanone is used in the examples and the reactions described are therefore not accompanied by the release of gaseous hydrogen.

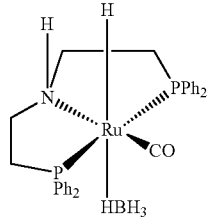

It is also known to use a ruthenium-based catalyst to carry out the dehydrogenative coupling of butanol using for example trans-RuH$_2$(CO)[HN(C$_2$H$_4$PiPr$_2$)$_2$], of formula D, (M. Bertoli, A. Choualeb, A. J. Lough, B. Moore, D. Spasyuk and D. Gusev, *Organometallics,* 2011, 30, 3479-3482) or [RuH(PNN)(CO)], of formula E, (cf. J. Zhang, G. Leitus, Y. Ben-David and D. Milstein, *J. Am. Chem. Soc.,* 2005, 127,10840-10841) in the presence of solvent and in the absence of base and hydrogen acceptor. However, these catalysts require long reaction times and high catalytic loadings in order to obtain yields of at most 90% ester.

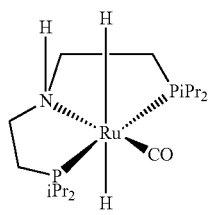

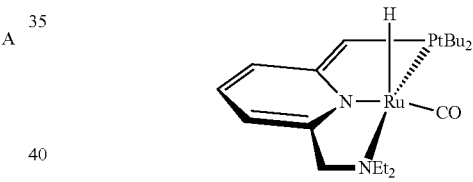

Implementing such methods on the industrial scale, however, presents numerous disadvantages. One of these disadvantages is the need to carry out several purification steps in order to isolate the products of the reaction which makes the method significantly more complex. Another problem is the use of organic products, such as solvents, in addition to the starting products. The use of such products substantially increases the environmental impact of such syntheses, which should of course be avoided. A method has now been achieved that solves these problems and that thus offers a realistic alternative to the industrial methods for synthesizing esters using fossil resources. This method makes it possible to combine high yields with simplified synthesis and purification steps in the implementation.

SUMMARY OF THE INVENTION

According to one embodiment, the invention relates to a method for synthesizing a second ester from a first ester, which method comprises the following steps:

a) bringing a first ester and a catalyst of formula 1 and dihydrogen into contact in order to obtain a first alcohol and a second alcohol;

b) separating said second alcohol from the reaction medium;

c) reacting, for example by heating, said first alcohol with said catalyst of formula 1 in order to obtain a second ester and dihydrogen; and d) recycling the dihydrogen obtained in step c) by introducing it into step a);

said formula 1 being:

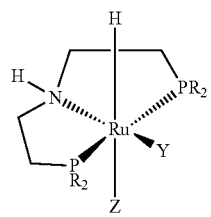

where R are groups, which may be identical or different, selected from the group consisting of cyclohexyl, phenyl, isopropyl and ethyl;

where Y is a $PR'_3$ phosphine, a CO radical or a hydrogen atom, R', which are identical or different, being $C_1$-$C_{12}$ alkyl groups or $C_6$-$C_{12}$ aryl groups; and where Z is a hydrogen atom, a $HBH_3$ group or a halogen atom.

According to one preferred embodiment of the invention, step c) is carried out without addition of a hydrogen acceptor. Advantageously, the steps a) to c) are carried out without additional addition of a hydrogen acceptor.

According to one preferred embodiment of the invention, step c) is carried out without addition of solvent. Advantageously, the steps a) to c) are carried out without addition of solvent.

According to one preferred embodiment of the invention, step c) is carried out without addition of base. Advantageously, the steps a) to c) are carried out without addition of base.

According to one preferred embodiment of the invention, step c) is carried out without addition of solvent, without addition of a hydrogen acceptor and without addition of base at the same time.

The expression "hydrogen acceptor" denotes the organic compounds that are capable of reacting with molecular hydrogen, $H_2$, in order to form a novel compound under the reaction conditions for ester synthesis. In particular, it may be compounds such as ketones, aldehydes and alkenes.

The absence of compounds that can react with the molecular hydrogen in order to absorb it in step c) is particularly advantageous since it enables in particular the production of gaseous hydrogen $H_2$ which is easily isolated from the reaction medium and which can thus be used subsequently, for example for step a). Furthermore, this avoids the stoichiometric formation of the hydrogenation product of the hydrogen acceptor, facilitating the downstream purification steps.

Thus, the method according to the invention also makes it possible to obtain gaseous molecular hydrogen. This is separated from the reaction medium by simple phase separation and may be discharged and/or collected directly, then reused in step a) of the method. This method is therefore particularly suitable for an industrial production device since it enables a simple and effective recycling of the by-products of the reaction, thus limiting the need for additional hydrogen for the first step.

The term "base" denotes a compound capable of capturing one or more protons. Within the context of the invention, the term base very particularly denotes bases such as sodium hydroxide, or alkoxylated alkali metal salts such as EtONa, MeONa or $^t$BuOK.

Preferably, the reaction is carried out in the absence of toluene or of xylene and in particular of solvent.

The term solvent denotes a substance, liquid at its usage temperature, which has the property of dissolving, diluting or extracting the alcohols and optionally the catalyst without chemically modifying them under the reaction conditions for the synthesis of esters. Optionally, a solvent is not modified itself under the conditions of the reaction in which it participates. It may be compounds such as water, inorganic solvents, and organic solvents of hydrocarbon-based, oxygenated and halogenated type.

The solvent, in the absence of which the reaction is carried out, may obviously also be a hydrogen acceptor and/or a base. Thus, within the context of the invention, the term solvent especially denotes ketones, such as 3-pentanone, acetone or cyclohexanone. It also denotes aromatic or aliphatic hydrocarbon-based compounds which are optionally halogenated, ethers and alcohols.

The expression "absence of" is used in its normal meaning which implies the absence, in the initial reaction mixture, of a sufficient amount of compound to play an effective role in the reaction and also the absence of external addition of this compound during the reaction. For example, the presence in the reaction medium of a minimum amount (for example in the form of a trace) of a hydrogen acceptor, of a base or of a solvent will not substantially influence the reaction. Thus, the absence of solvent implies the absence of an amount sufficient to dissolve/dilute/extract the starting product(s) (i.e. the ester(s) and the alcohol(s)) and also the catalyst. For a solvent, this amount is generally greater than the numbers of moles of reactants, that is to say that the solvent is generally present in the reaction medium in a molar concentration of greater than or equal to 50%.

Preferably, the expression "absence of" implies a molar concentration of said compound of less than 10%, and more particularly of less than 5%, or even the complete absence thereof, i.e. less than 0.001%.

Preferably, in the formula 1 of the catalyst, Z is not a halogen atom.

Preferably, the R' group from the formula 1 is a methyl, ethyl, isopropyl or phenyl group. It is also preferred for the R' groups to be identical.

Advantageously, the four R groups are identical.

Preferably, R is a cyclohexyl or isopropyl group.

According to one particular embodiment of the invention, the first ester, or starting ester, has the following formula:

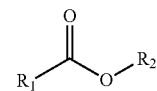

where $R_1$ is a linear or branched $C_2$ to $C_{32}$, preferably $C_2$ to $C_{22}$ alkyl group, and $R_2$ is a $C_1$ to $C_6$ alkyl group. $R_1$ and $R_2$ may also comprise unsaturations or functionalizations such as hydroxyl, amine and ketone groups:

The starting ester, or first ester, may also have the following formula:

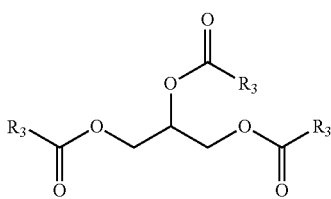

where $R_3$ are identical or different, linear or branched, $C_2$ to $C_{32}$, preferably $C_8$ to $C_{22}$ alkyl groups. $R_3$ may also comprise unsaturations or functionalizations such as, for example, at least one hydroxyl, amine or ketone group.

For example, the first ester may be a fatty acid methyl ester (FAME) such as methyl oleate.

Preferably, the catalyst loading used in the method according to the invention, and more particularly in steps a) and c), is less than 10 000 ppm, more particularly less than 1000 ppm, even more particularly less than 500 ppm. This loading may for example be around 50±10 ppm.

Preferably, the catalyst loading used in the method according to the invention is selected from a range extending from 10 000 ppm to 1 ppm, more particularly from 1000 ppm to 10 ppm, even more particularly from 500 ppm to 50 ppm. This loading may for example be around 225±10 ppm. Advantageously, the loading is selected from a range extending from 500 ppm to 1 ppm, advantageously from 200 ppm to 20 ppm, more advantageously from 60 ppm to 40 ppm.

The above proportions are given relative to the total mass of the starting products.

Preferably, step a) is carried out under pressure of gaseous hydrogen, said hydrogen pressure possibly being selected from the range of from 10 to 50 bar, preferably from 20 to 30 bar, for example at a pressure of around 20 bar.

Step a) is carried out at a temperature ranging from 5° C. to 150° C., advantageously from 75° C. to 125° C., more advantageously at 100° C.

Advantageously, the isolation step b) is carried out by known separation techniques such as vacuum evaporation or aqueous extraction. Since the product of the reaction generally comprises a second, unwanted alcohol, this is advantageously extracted from the reaction medium. Thus, the subsequent esterification reaction makes it possible to couple 2 molecules of the same alcohol in order to create a new ester, different from the starting ester.

Preferably, step c) comprises the heating of the reaction medium and is carried out at a temperature selected from a temperature range extending from 200° C. to 15° C., more particularly from 150° C. to 40° C. and even more particularly from 130° C. to 80° C. This temperature may be around 130±1° C. Preferably, the temperature may range from 5° C. to 200° C., advantageously from 100° C. to 150° C., more advantageously at around 130° C.

Preferably, the reaction of step c) is carried out at a pressure ranging from 20 bar to 1 bar. Advantageously, no particular pressure is applied and the reaction is carried out at atmospheric pressure or in an open system.

It is advantageous for the pressure to allow a release of hydrogen. Thus an atmospheric pressure, or a pressure below atmospheric pressure (referred to as under vacuum).

Preferably, the catalyst used in steps a) and c) of the method is preferably the same.

In the method according to the invention, the starting compound (ester) may be present alone or as a mixture with other reactants such as other esters.

Furthermore, the starting compound may be used in purified form or in crude, especially unrefined, form, in particular when the compound is obtained from vegetable oils (e.g. from oleaginous materials).

According to one particular aspect of the invention, step c) of the method, and preferably all the steps a) to c), is/are carried out in the absence of any additive (other than the catalyst) that may have an effect on the coupling reaction of the alcohol and/or on the production of molecular hydrogen.

According to another preferred aspect of the invention, the method does not comprise a step of drying and/or degassing starting products or the reaction medium. This is because it has surprisingly been determined that the catalyst (and particularly the catalysts where Z is $HBH_3$ such as Ru-MACHO-BH, of formula C or 1a)) remains active in the presence of air and traces of water.

Indeed it appears that, unexpectedly, these specific reaction conditions, especially without addition of solvent, without addition of hydrogen acceptor, without addition of base, in the presence of air and traces of water, make it possible to simultaneously obtain a shorter reaction time and the use of a very reduced catalyst loading while retaining a high yield. The fact of being able to dispense with the use of additional chemical compounds such as those mentioned above makes it possible to reduce the manufacturing costs, to avoid the corrosion problems linked to their use and therefore to drastically reduce the environmental impact of such methods. This also makes it possible to greatly simplify the operations for separating and/or purifying the products of the reaction downstream of the method, operations such as the elimination of the solvent of the reaction by distillation, the neutralization of the reaction medium using a base, or the separation of the more numerous products of the reaction during the use of a hydrogen acceptor.

According to one particular aspect of the invention, the catalyst is preferably a catalyst of formula 1 in which Z is $HBH_3$ and/or Y is a CO radical and the R radicals are phenyl radicals.

According to one aspect of the invention, the catalyst is preferably a catalyst of formula 1 in which the four R radicals are identical.

According to one particularly preferred aspect of the invention, the catalyst used is a catalyst of formula 1 in which the Z group is H and the Y group is a $PR'_3$ phosphine where R' is a $C_1$-$C_{12}$ alkyl group or $C_6$-$C_{12}$ aryl group, in particular a methyl, ethyl, isopropyl or phenyl group.

According to one preferred variant of the invention, the catalyst is the catalyst of formula 1b (R=i-Pr, Z=$HBH_3$, Y=CO).

According to one preferred variant of the invention, the catalyst is the catalyst of formula 1a or C (R=Ph, Z=$HBH_3$, Y=CO).

According to one preferred variant of the invention, the catalyst is the catalyst of formula 1c (R=Cy, Z=$HBH_3$, Y=CO).

According to one preferred variant of the invention, the catalyst is the catalyst of formula 6a (R=Ph, Z=H, Y=CO).

According to one preferred variant of the invention, the catalyst is the catalyst of formula 6b (R=isopropyl, Z=H, Y=CO).

According to one preferred variant of the invention, the catalyst is the catalyst of formula 6c (R=Cy, Z=H, Y=CO).

The invention also relates to the catalysts described in this application as such and also to the methods for the manufacture thereof. In particular, a complex of formula 1c, 1b, 6a and 6c, and also a complex of the same formula where the carbonyl substituent is substituted by a phosphine is one subject of the invention. The uses thereof in catalytic synthesis methods and such methods are also is also subjects of the invention.

The invention also relates to an ester obtained directly by the method described above.

According to another embodiment of the invention, the method is a method for synthesizing cerides.

According to another embodiment, it can also be envisaged to use, in step a) and c), catalysts of formulae 1 that are different. It can likewise be envisaged to use the alcohol extracted from step b) as starting product for the synthesis of the second ester.

DETAILED DESCRIPTION OF THE INVENTION

Example 1a

Synthesis of Oleyl Oleate (a Ceride) from a Methyl Ester Using the Catalyst 1a

The reaction scheme for the reaction is the following:

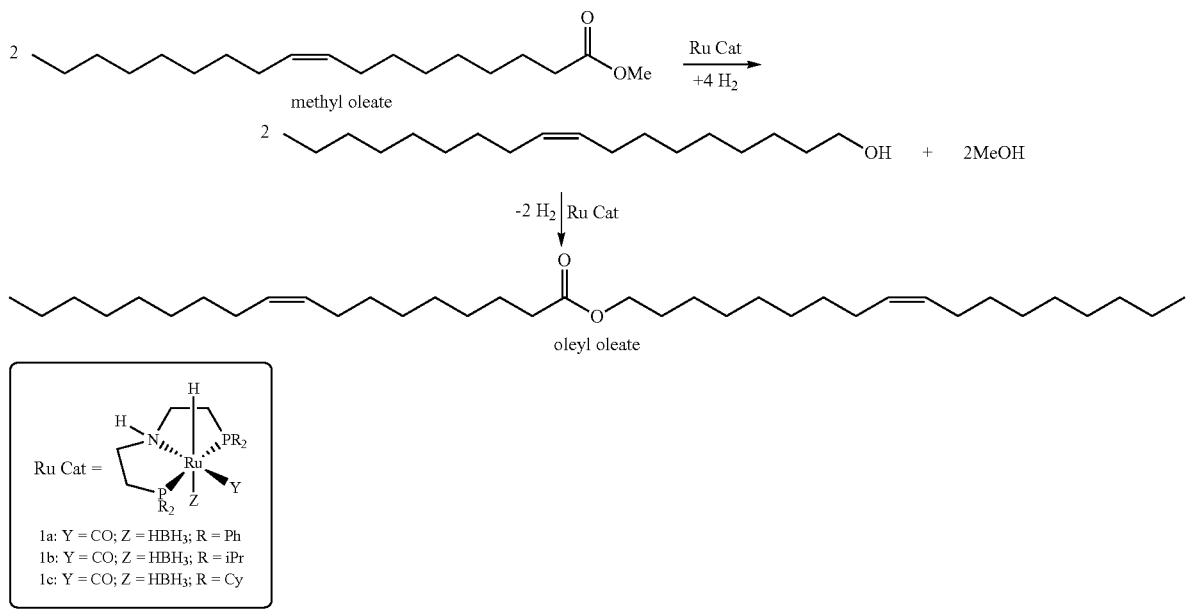

The catalyst 1a (4.5 mg; 7.7 µmol) is introduced into an autoclave containing a stirrer bar. 2.3 g of methyl oleate (7.7 mmol) is introduced via a syringe under an argon atmosphere. The autoclave is then purged three times by a vacuum/hydrogen cycle and then around 20 bar of hydrogen are introduced. The system is heated to 100° C. with the aid of an oil bath and is stirred magnetically for 18 hours. Methanol and also oleyl alcohol are obtained.

It is noted that the unsaturations of the fatty chain are not hydrogenated during this process.

Example 1b

Synthesis of Oleyl Oleate (a Ceride) from a Methyl Ester Using the Catalyst 1b

The reaction scheme for the reaction is the following:

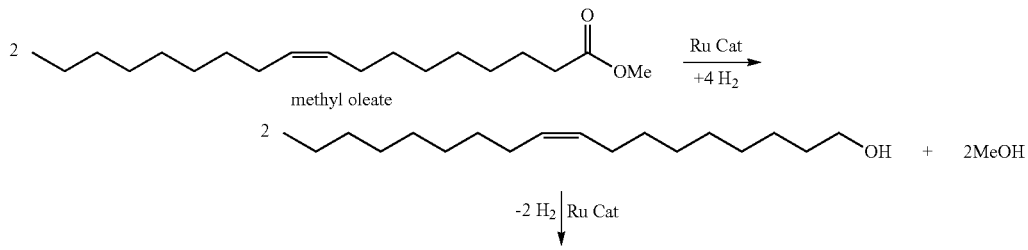

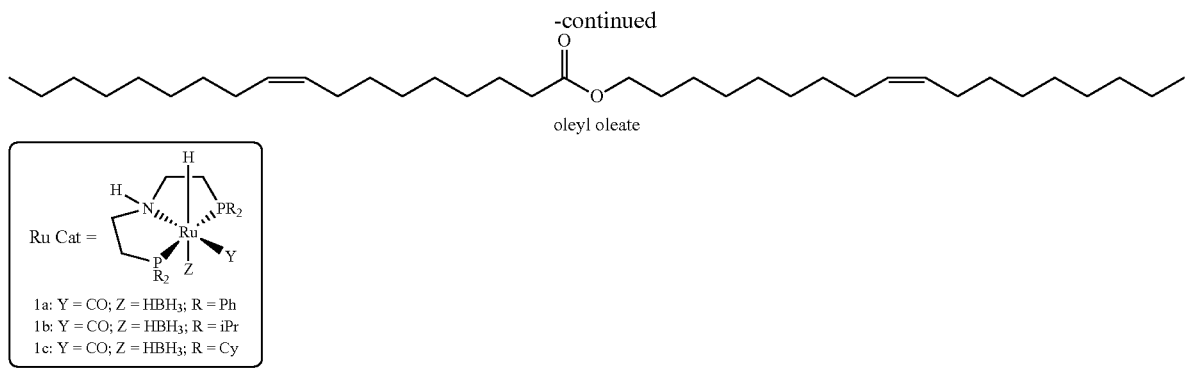

oleyl oleate

The catalyst 1b (3.4 mg; 7.7 µmol) is introduced into an autoclave containing a stirrer bar. 2.3 g of methyl oleate (7.7 mmol) is introduced via a syringe under an argon atmosphere. The autoclave is then purged three times by a vacuum/hydrogen cycle and then around 20 bar of hydrogen are introduced. The system is heated to 100° C. with the aid of an oil bath and is stirred magnetically for 18 hours. Methanol and also oleyl alcohol are obtained. It is noted that the unsaturations of the fatty chain are not hydrogenated during this process.

Example 1c

Synthesis of Oleyl Oleate (a Ceride) from a Methyl Ester Using the Catalyst 1c

The reaction scheme for the reaction is the following:

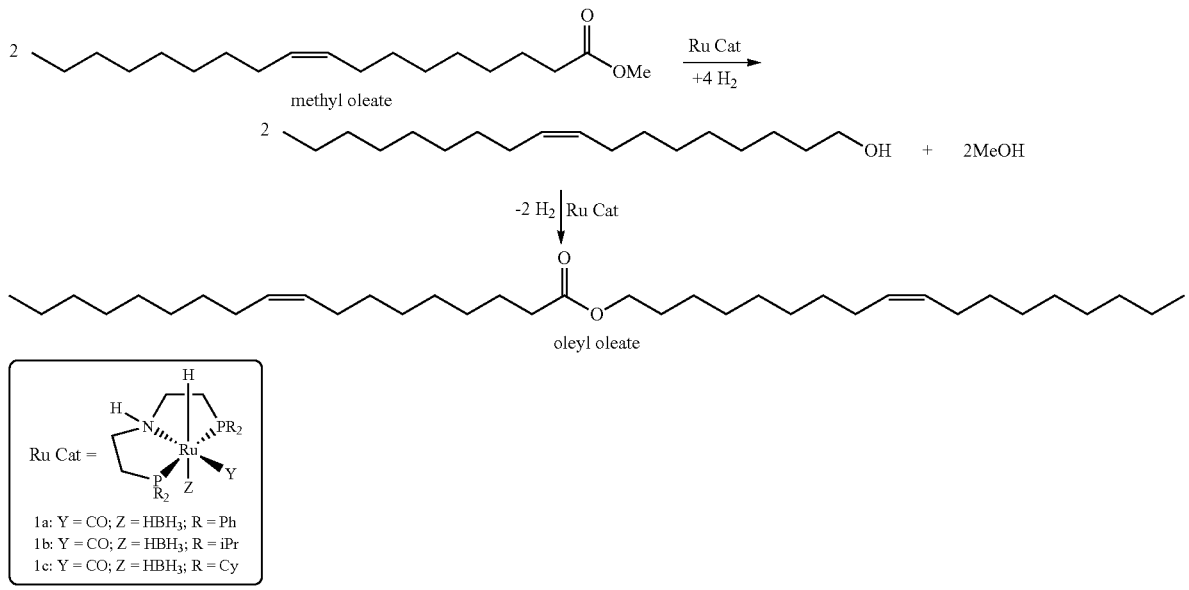

The catalyst 1c (4.7 mg; 7.7 µmol) is introduced into an autoclave containing a stirrer bar. 2.3 g of methyl oleate (7.7 mmol) is introduced via a syringe under an argon atmosphere. The autoclave is then purged three times by a vacuum/hydrogen cycle and then around 20 bar of hydrogen are introduced. The system is heated to 100° C. with the aid of an oil bath and is stirred magnetically for 18 hours. Methanol and also oleyl alcohol are obtained. It is noted that the unsaturations of the fatty chain are not hydrogenated during this process.

The selectivites and the degrees of conversion obtained in examples 1a, 1b and 1c are compiled in table I:

TABLE I

| Cat. (0.1 mol %) | Oleyl alcohol selectivity[a] | Oleyl oleate selectivity[a] | Conversion[b] |
|---|---|---|---|
| 1a | 80% | 20% | 93% |
| 1b | 76% | 24% | 92% |
| 1c | 73% | 27% | 93% |

[a]Selectivity and conversion determined by $^1$H NMR.
[b]Conversion of methyl oleate.

The reaction medium is transferred under argon with the aid of a syringe into a Schlenk tube. The methanol is evaporated under vacuum (20° C., 30 min, $1 \times 10^{-3}$ mbar). The Schlenk tube is then equipped with a condenser topped by a bubbler. The system still containing the dissolved catalyst 1a, 1b or 1c is then heated at 130° C. for 18 h. The concomitant release of gaseous molecular hydrogen is observed and can therefore be used in the synthesis of the fatty alcohol.

The products obtained are determined by NMR (Bruker Avance 1, 300 MHz, 5 mm probe NMR spectrometer) and are compiled in table II:

TABLE II

| Cat. (0.1 mol %) | Oleyl oleate selectivity | Methyl oleate selectivity | Conversion |
|---|---|---|---|
| 1a | 95% | 5% | 58% |
| 1b | 93% | 7% | 87% |
| 1c | 95% | 5% | 86% |

[a]Selectivity and conversion determined by $^1$H NMR.
[b]Conversion of oleyl alcohol.

This conversion makes it possible to directly obtain cerides from the methyl esters resulting from the transesterification of the triglycerides.

This methodology can be generalized to other fatty acid methyl esters (FAMEs) irrespective of the length of the carbon chain of the starting methyl esters.

Example 2

Synthesis of Cerides from a Triglyceride

Example 2a

Synthesis of Butyl Butyrate from Glyceryl Tributyrate (Tributyrin) in the Presence of a Solvent The synthesis of butyl butyrate was carried out in two steps using the same ruthenium catalyst: triglyceride hydrogenation followed by a dehydrogenation of the corresponding alcohol. The reaction scheme for the reaction is the following:

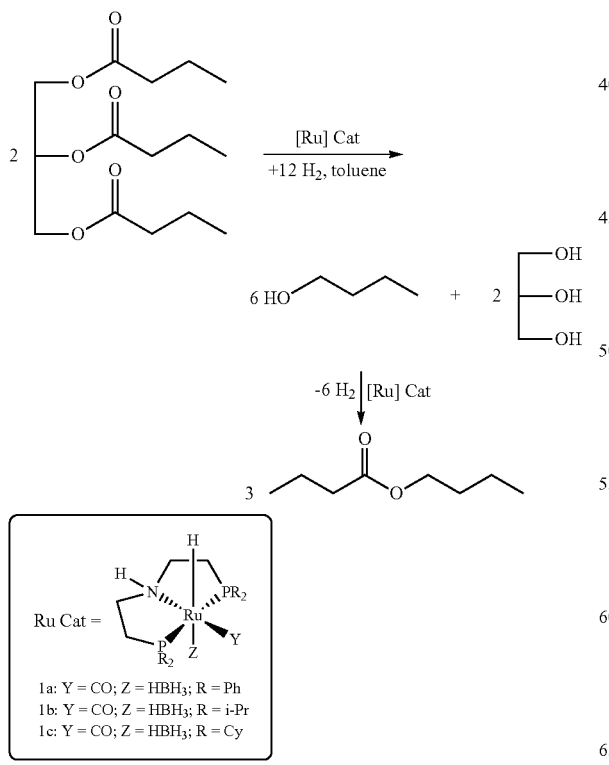

Step 1: In the glove box, 1 mol % of catalyst 1a (30 mg; 51.3 µmol), 0.516 g of glyceryl tributyrate (1.7 mmol) and toluene (7 ml) are successively loaded under an argon atmosphere into an autoclave containing a stirrer bar. The autoclave is then purged three times with hydrogen and then around 40 bar of hydrogen are introduced. The system is heated to 100° C. with the aid of an electric heating tape and is stirred magnetically for 18 hours. The reaction mixture was filtered through Celite if necessary before being analyzed by proton NMR and gas chromatography. The degree of conversion is of the order of 96%.

The yields for n-butanol and butyl butyrate are respectively 84% and 2%. Furthermore, the formation of monoester and diester glycerides is also observed with estimated percentages of the order of 3%.

Step 2: In the glove box, the reaction medium is transferred under an argon atmosphere with the aid of a syringe into a Schlenk tube. The Schlenk tube is then equipped with a condenser topped by a bubbler. The system is then heated at 120° C. for 18 h. The products obtained are determined by NMR and the percentage of each product is estimated by proton NMR and gas chromatography. The degree of conversion of n-butanol is of the order of 20%. The selectivity for butyl butyrate is 100%.

Example 2b

Synthesis of Butyl Butyrate from Glyceryl Tributyrate (Tributyrin) in the Absence of Solvent The reaction scheme for the reaction is the following:

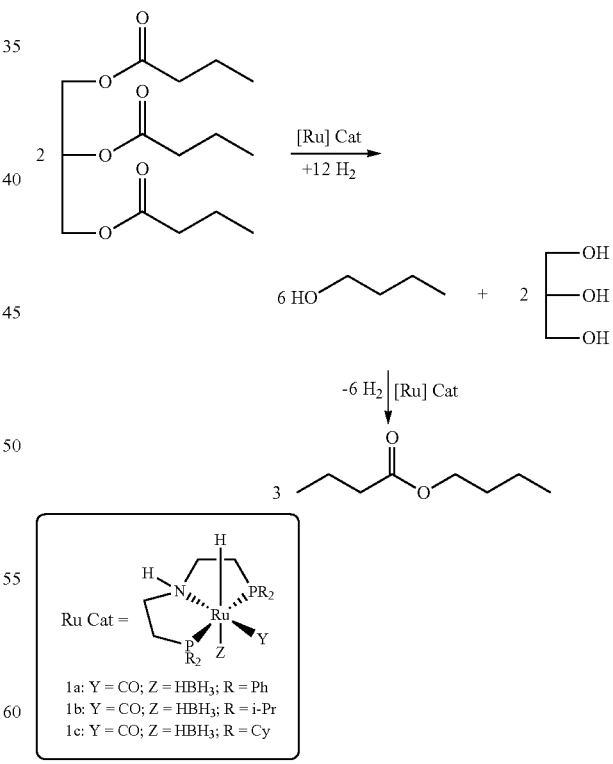

Step 1: In the glove box, 0.1 mol % of catalyst 1a (30 mg; 51.3 µmol), 5.16 g of glyceryl tributyrate (1.7 mmol) are successively loaded under an argon atmosphere into an autoclave containing a stirrer bar. The autoclave is then purged three times with hydrogen and then around 40 bar of hydrogen are introduced. The system is heated to 100° C. with the aid of an electric heating tape and is stirred magnetically for 18 hours. The reaction mixture is analyzed by proton NMR and gas chromatography. The degree of conversion is of the order of 84%. The yields for n-butanol and butyl butyrate are respectively 45% and 7%. Furthermore, the formation of monoester and diester glycerides is also observed with estimated percentages of the order of 16% and 13% respectively.

Step 2: In the glove box, the reaction medium is transferred under argon with the aid of a syringe into a Schlenk tube. The Schlenk tube is then equipped with a condenser topped by a bubbler. The system is then heated at 120° C. for 18 h. The products obtained are determined by NMR and the percentage of each product is estimated by proton NMR and gas chromatography. The degree of conversion of n-butanol is of the order of 5%. The selectivity for butyl butyrate is 100%.

Example 2c

Synthesis of Oleyl Oleate from Glyceryl Trioleate (Triolein)

The reaction scheme for the reaction is the following:

Step 1: In the glove box, 0.33 mol % of catalyst 1a (3.0 mg; 5.13 µmol), 0.453 g of glyceryl tributyrate (0.51 mmol) and toluene (7 ml) are successively loaded under an argon atmosphere into an autoclave containing a stirrer bar.

The autoclave is then purged three times with hydrogen and then around 40 bar of hydrogen are introduced. The system is heated to 100° C. with the aid of an electric heating tape and is stirred magnetically for 18 hours. The reaction mixture is analyzed by proton NMR and gas chromatography. The degree of conversion is of the order of 94%. The yields for oleyl alcohol and oleyl oleate are respectively 87% and 7%. It is interesting to note that the unsaturations of the fatty chain are not hydrogenated during this process.

Step 2: In the glove box, the reaction medium is transferred under argon with the aid of a syringe into a Schlenk tube. A further 0.66 mol% of catalyst 1a was added (6.0 mg; 10.26 µmol). The Schlenk tube is then equipped with a condenser topped by a bubbler. The system is then heated at 120° C. for 18 h. The products obtained are determined by NMR and the percentage of each product is estimated by proton NMR and gas chromatography. It should be noted that the monoester and diester glycerides are only present in the form of traces.

The yields and the degrees of conversion obtained in examples 2a, 2b and 2c after two steps are compiled in table III:

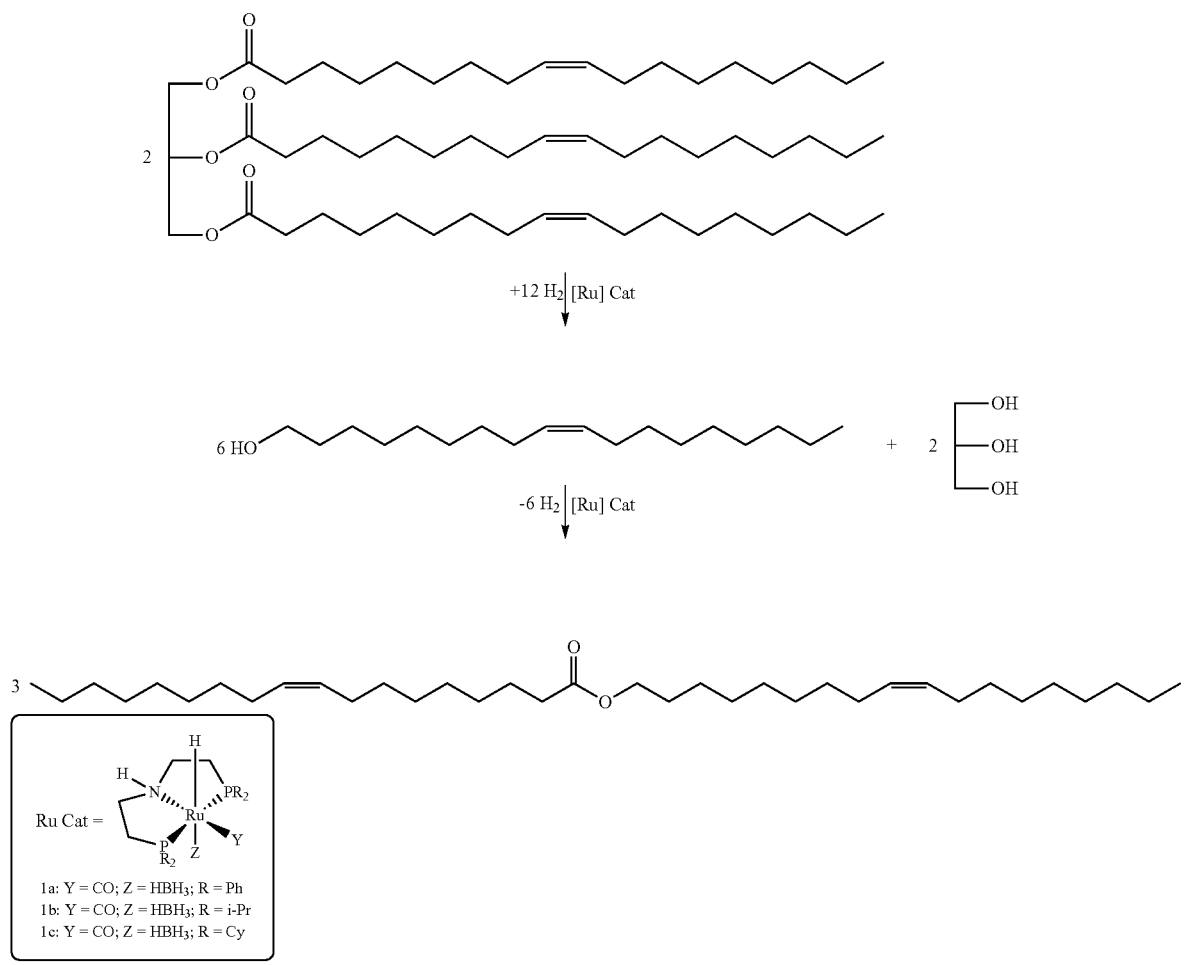

TABLE III

| Cat.* | Substrate | Solvent | Yield Alcohol[b] | Yield Ceride[b] | Conversion[b] |
|---|---|---|---|---|---|
| 1a, 1 mol % | Tributyrin | Toluene | 72% | 21% | 96% |
| 1a, 0.1 mol % | Tributyrin | No | 43% | 10% | 84% |
| 1a,[a] (0.33 mol %) + 0.66 mol % | Triolein | Toluene | 87% | 7% | 94% |

*Catalyst/ester function ratio;
[a]0.33 mol % of catalyst 1a was used for the first step; a further 0.66 mol % of 1a was added to the reaction medium for the second step.
[b]Yields and conversions estimated by $^1$H NMR and GC.

Example 3

Synthesis of carbonylchlorohydrido[bis(2-diisopropyl-phosphinoethyl)amino]ruthenium(II) (2b)

The reaction scheme for the reaction is the following:

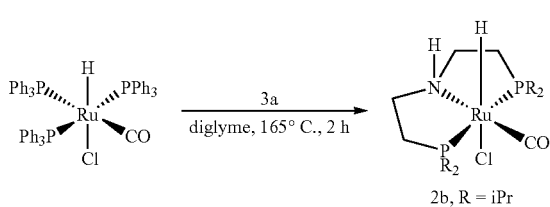

Synthesis: In a Schlenk tube a suspension of carbonylchlorohydrido[tris(triphenylphosphine)]ruthenium(II) (Strem Chemicals, 0.999 g; 1.04 mmol) and of NH($C_2H_4PiPr_2$)$_2$, 3a (0.357 g; 1.17 mmol) in diglyme (10 ml) is placed in an oil bath preheated to 165° C. and left stirring for two hours to give a clear yellow solution. The solution is left for 18 h at ambient temperature to give a precipitate. 10 ml of pentane are added and the suspension is cooled to 0° C. for 1 hour. The supernatant is then removed and the crystals are washed with diethyl ether (3×5 ml) and then dried under reduced pressure to give the desired product in the form of a very pale yellow powder. Yield: 64% (0.317 g).

$^{31}$P-{$^1$H} NMR (CD$_2$Cl$_2$, 121.5 MHz): δ. 74.7 ppm. $^1$H and $^{31}$P NMR in agreement with the spectral data from the literature. See: Bertoli, M.; Choualeb, A.; Lough, A. J.; Moore B.; Spasyuk, D.; Gusev D. G. *Organometallics*, 2011, 30, 3479.

Example 4

Synthesis of carbonylchlorohydrido[bis(2-dicyclohexyl-phosphinoethyl)amino]ruthenium(II) (2c)

The reaction scheme for the reaction is the following:

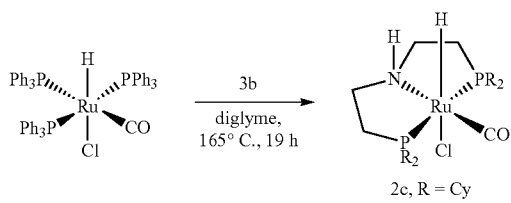

Synthesis: In a Schlenk tube a suspension of carbonylchlorohydrido[tris(triphenylphosphine)]ruthenium(II) (Strem Chemicals, 1.000 g; 1.05 mmol) and of NH($C_2H_4PCy_2$)$_2$, 3b (0.498 g; 1.07 mmol) in diglyme (10 ml) is placed in an oil bath preheated to 165° C. and left stirring for 19 hours to give a suspension. The medium is then cooled to ambient temperature, the supernatant is removed and the precipitate is washed with diethyl ether (3×5 ml) and then dried under reduced pressure to give the desired product in the form of a very pale yellow powder. Yield: 78% (0.518 g). $^{31}$P-{$^1$H} NMR (CD$_2$Cl$_2$, 121.5 MHz): δ. 65.6 ppm. $^1$H and $^{31}$P NMR in agreement with the spectral data from the literature. See: Nielsen, M.; Alberico, E.; Baumann, W.; Drexler H.-J.; Junge, H.; Gladiali, S.; Beller, M. Nature, 2013, (doi:10.1038/nature11891).

Example 5

Synthesis of carbonylhydrido(tetrahydroborato)[bis(2-di-i-propylphosphinoethyl)amino]ruthenium(II) (1b)

The reaction scheme for the reaction is the following:

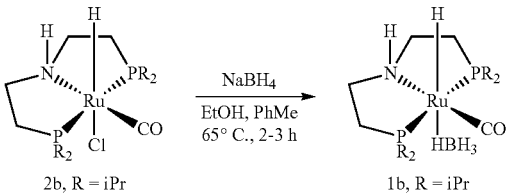

Synthesis: In a Schlenk tube under a stream of argon, a solution of NaBH$_4$ (5 mg; 0.24 mmol) in ethanol (2 ml) is added to a suspension of carbonylchlorohydrido[bis(2-di-i-propylphosphinoethyl)amino]ruthenium (II), 2b, (50 mg; 0.08 mmol) in toluene (8 ml). The Schlenk tube is then hermetically sealed, immersed in an oil bath preheated to 65° C. and left stirring for 2 h 30 min to give an opalescent solution. The solvent is then removed by distillation under reduced pressure (ambient temperature, 1×10$^{-3}$ mbar). The white residue obtained is extracted using dichloromethane (3×5 ml) and filtered over a sintered glass. The filtrate is then concentrated under reduced pressure (ambient temperature, 1×10$^{-3}$ mbar) to give the desired product in the form of a white powder (30 mg; yield: 62%).

$^1$H NMR (CD$_2$Cl$_2$, 300 MHz): δ. 3.90 (broad; 1H; NH); 3.30-3.12 (m, 2H); 2.56-2.44 (m, 2H); 2.30-2.21 (m, 2H); 1.94-1.82 (m, 2H); 1.38 (dd; J$_{HP}$=16.2 Hz; J$_{HH}$=7.5 Hz; 6H); 1.28-1.14 (m, 18 H); −1.92-−2.69 (broad; 4H; RuHBH$_3$); −13.53 (t, J$_{HP}$=17.7 Hz; 1H; RuH). $^{31}$P-{$^1$H} NMR (CD$_2$Cl$_2$, 121.5 MHz): δ. 77.7 ppm.

Example 6

Synthesis of Carbonylhydrido(Tetrahydroborato)[bis(2-dicyclohexylphosphinoethyl)amino]ruthenium(II) (1c)

The reaction scheme for the reaction is the following:

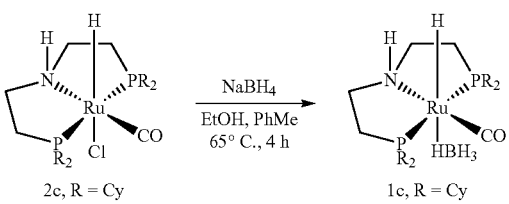

Synthesis: In a Schlenk tube under a stream of argon, a solution of $NaBH_4$ (48 mg; 1.37 mmol) in ethanol (12 ml) is added to a suspension of carbonylchlorohydrido[bis(2-dicyclohexylphosphinoethyl)amino]ruthenium (II), 2c, (200 mg; 0.43 mmol) in toluene (16 ml). The Schlenk tube is then hermetically sealed, immersed in an oil bath preheated to 65° C. and left stirring for four hours to give an opalescent solution. The solvent is then removed by distillation under reduced pressure (ambient temperature, $1 \times 10^{-3}$ mbar). The white residue obtained is extracted using dichloromethane (3×5 ml) and filtered over a sintered glass. The filtrate is then concentrated under reduced pressure (ambient temperature, $1 \times 10^{-3}$ mbar) to give the desired product in the form of a white powder (171 mg; yield: 88%).

$^1$H NMR ($CD_2Cl_2$, 300 MHz): δ. 3.85 (broad; 1H; NH); 3.27-3.09 (m, 2H); 2.27-2.10 (m, 8H); 1.96-1.68 (m; 20H); 1.61-1.20 (m, 22H); −2.19−−2.50 (broad; 4H; $RuHBH_3$); −13.60 (t, $J_{HP}$=17.9 Hz; 1H, RuH). $^{31}$P-{$^1$H} NMR ($CD_2Cl_2$, 121.5 MHz): δ. 68.9 ppm.

Example 7

Synthesis of carbonyl(dihydrido)[bis(2-diisopropyl-phosphinoethyl)amino]ruthenium(II) (6b)

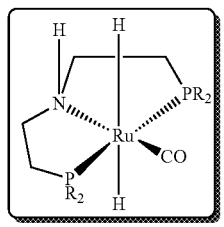

6b: R = iPr

Synthesis: In a Schlenk tube a whitish suspension of carbonylhydridochloro[bis(2-diisopropylphosphinoethyl)amino]ruthenium(II) 2b (221 mg; 0.468 mmol) in THF (8 ml) is treated with a 1 M commercial solution of $NaHBEt_3$ in toluene (0.45 ml; 0.450 mmol). Next, the medium is left stirring at ambient temperature under an argon atmosphere for 18 hours to give an opalescent light yellow solution. The solution is then concentrated under reduced pressure to result in a yellow solid residue which is dissolved with toluene (8 ml). This new solution is filtered over sintered glass and concentrated under reduced pressure to give a yellow powder. Yield: 89% (181 mg).

$^1$H NMR ($C_6D_6$, 300 MHz): δ. 2.20-2.04 (m, 3H); 1.92-1.83 (m, 4H); 1.66-1.54 (m, 2H); 1.36-1.27 (m, 24H); 1.01-0.91 (m, 2H); −6.18−−6.46 (m, 2H; $RuH_2$).

$^{31}$P-{$^1$H} NMR ($C_6D_6$, 121.5 MHz): δ. 91.1 ppm.

Example 8

Synthesis of carbonyl(dihydrido)[bis(2-dicyclo-hexyl-phosphinoethyl)amino]ruthenium(II) (6c)

Synthesis: In a Schlenk tube a whitish suspension of carbonylhydridochloro[bis(2-dicyclohexylphosphinoethyl)amino]ruthenium(II) 2c (63 mg; 0.1 mmol) in THF (2 ml) is treated with a 1 M commercial solution of $NaHBEt_3$ in toluene (0.12 ml; 0.12 mmol). Next, the medium is left stirring at ambient temperature under an argon atmosphere for 18 hours to give an opalescent light yellow solution. The solution is then concentrated under reduced pressure to result in a yellow solid residue which is dissolved with toluene (2 ml). This new solution is filtered over sintered glass and concentrated under reduced pressure to give a yellow powder. Yield: 80% (48 mg).

$^1$H NMR ($C_6D_6$, 300 MHz): δ. 2.32-2.07 (m, 6H); 1.90-1.60 (m, 31H), 1.34-1.03 (m, 16H); −6.18−−6.34 (m, 2H; $RuH_2$).

$^{31}$P-{$^1$H} NMR ($C_6D_6$, 121.5 MHz): δ. 80.4 ppm.

The invention is not limited to the embodiments presented and other embodiments will become clearly apparent to a person skilled in the art.

The invention claimed is:

1. A method for synthesizing a second ester from a first ester which comprises the following steps:
   a) bringing a first ester and a catalyst of formula 1 and dihydrogen into contact in order to obtain a first alcohol and a second alcohol;
   b) separating said second alcohol from the reaction medium;
   c) reacting said first alcohol with the catalyst of formula 1 from step a) in order to obtain a second ester and dihydrogen; and
   d) recycling the dihydrogen obtained in step c) by introducing it into step a);

said formula 1 being:

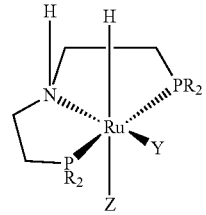

where R are groups, which may be identical or different, selected from the group consisting of cyclohexyl, phenyl, isopropyl and ethyl;

where Y is a $PR'_3$ phosphine, a CO radical or a hydrogen atom, R', which are identical or different, being $C_1$-$C_{12}$ alkyl groups or $C_6$-$C_{12}$ aryl groups; and where Z is a hydrogen atom, a $HBH_3$ group or a halogen atom.

2. The method as claimed in claim 1, wherein step c) of the method is carried out without addition of a hydrogen acceptor.

3. The method as claimed in claim 1, wherein the step(s) a) and/or c) of the method is/are carried out without addition of solvent.

4. The method as claimed in claim 3, wherein the step(s) a) and/or c) of the method is/are carried out without addition of base.

5. The method as claimed in claim 1, wherein Z is not a halogen atom.

6. The method as claimed in claim 1, wherein the R' group is a methyl, ethyl, isopropyl or phenyl group.

7. The method as claimed in claim 1, wherein R is a cyclohexyl or isopropyl group.

8. The method as claimed in claim 1, wherein said first ester has the following formula:

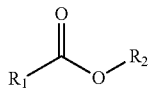

where $R_1$ is a $C_2$ to $C_{32}$ alkyl group, and $R_2$ is a $C_1$ to $C_6$ alkyl group.

9. The method as claimed in claim 1, wherein said first ester has the following formula:

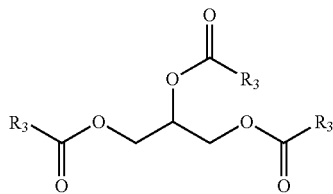

where $R_3$ are identical or different $C_2$ to $C_{32}$ alkyl groups.

10. The method as claimed in claim 1, wherein the loading of said catalyst of formula 1 used in step b) is selected from a range extending from 500 ppm to 1 ppm.

11. The method as claimed in claim 1, wherein step a) is carried out under reaction conditions comprising:
i) a temperature ranging from 5° C. to 150° C.
ii) a pressure of dihydrogen ranging from 1 bar to 50 bar.

12. The method as claimed in claim 1, wherein step c) is carried out under reaction conditions comprising:
i) a temperature ranging from 5° C. to 200° C.;
ii) a pressure that allows the concomitant release of hydrogen.

13. The method as claimed in claim 12, wherein said pressure that allows the release of hydrogen is a pressure equal to or below atmospheric pressure.

14. A method of catalytic synthesis, comprising the use of a catalyst of formula 1:

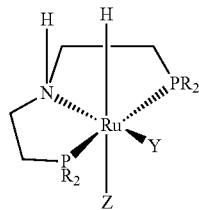

where R are groups, which may be identical or different, selected from the group consisting of cyclohexyl, phenyl, isopropyl and ethyl;
where Y is a $PR'_3$ phosphine, a CO radical or a hydrogen atom, R', which are identical or different, being $C_1$-$C_{12}$ alkyl groups or $C_6$-$C_{12}$ aryl groups; and
where Z is a hydrogen atom, a $HBH_3$ group or a halogen atom, in order to carry out a catalytic synthesis, said synthesis comprising the following steps:
a) bringing a first ester and a catalyst of formula 1 and dihydrogen into contact in order to obtain a first alcohol and a second alcohol;
b) separating said second alcohol from the reaction medium.

15. The method as claimed in claim 14, wherein said first ester is a fatty acid methyl ester.

16. The method as claimed in claim 11, wherein step a) is carried out under reaction conditions comprising:
i) a temperature ranging from 75° C. to 125° C.;
ii) a pressure of dihydrogen ranging from 1 bar to 50 bar.

17. The method as claimed in claim 11, wherein step a) is carried out under reaction conditions comprising:
i) a temperature ranging from 5° C. to 150° C.; and
ii) a pressure of dihydrogen ranging 10 to 30 bar.

18. The method as claimed in claim 11, wherein step a) is carried out under reaction conditions comprising:
i) a temperature ranging from 75° C. to 125° C.; and
ii) a pressure of dihydrogen ranging 10 to 30 bar.

19. The method as claimed in claim 10, wherein the loading of said catalyst of formula 1 used in step b) is selected from a range extending from 200 ppm to 20 ppm.

20. The method as claimed in claim 12, wherein step c) is carried out under reaction conditions comprising:
i) a temperature ranging from 100° C. to 150° C.;
ii) a pressure that allows the concomitant release of hydrogen.

* * * * *